United States Patent [19]
Stenoien et al.

[11] Patent Number: 5,840,240
[45] Date of Patent: Nov. 24, 1998

[54] METHOD OF MAKING A SILICONE COMPOSITE VASCULAR GRAFT

[75] Inventors: Mark D. Stenoien, Columbia Heights; William J. Drasler, Minnetonka; Robert J. Scott, Oak Grove; Mark L. Jenson, Greenfield, all of Minn.

[73] Assignee: Possis Medical, Inc., Minneapolis, Minn.

[21] Appl. No.: 552,930

[22] Filed: Nov. 3, 1995

Related U.S. Application Data

[63] Continuation of Ser. No. 787,227, Nov. 4, 1991, abandoned.

[51] Int. Cl.$^6$ ........................................................ A61F 2/06
[52] U.S. Cl. .......................... 264/425; 264/413; 264/441; 264/465; 623/1
[58] Field of Search ............................... 264/24, 234, 235, 264/413, 425, 441, 465; 623/1

[56] References Cited

U.S. PATENT DOCUMENTS 4,878,908  11/1989  Martin et al. ................................ 623/1

*Primary Examiner*—Christopher Raimund
*Attorney, Agent, or Firm*—Hugh D. Jaeger

[57] ABSTRACT

A silicone/DACRON polyester composite vascular graft especially well suited as an arteriovenous (A-V) graft fistula for dialysis application. The graft has the ability to seal around needle puncture holes without externally applied pressure, excellent anti-kink, anti-crush and strength properties, and a smooth non-porous inner surface which reduces thrombus deposition and enhances the graft wall compliance or elasticity.

19 Claims, 2 Drawing Sheets

METHOD OF MAKING A SILICONE COMPOSITE VASCULAR GRAFT

This application is a contunuation of application Ser. No. 07/787,227, filed Nov. 4, 1991, abandoned.

BACKGROUND OF THE INVENTION

1. Field of the Invention

The present invention pertains to a silicone/DACRON® composite vascular graft, especially well suited as an arteriovenous (A-V) graft fistula for patients requiring long-term vascular access, such as in the case of chronic kidney dialysis.

2. Description of the Prior Art

Other silicone grafts have been developed in the past using a variety of construction methods. The benefits of silicone material were described in U.S. Pat. No. 4,687,482. A DACRON outer support, which prevents aneurysm is described in U.S. Pat. Nos. 4,657,544 and 4,629,458. White and Roy have patents which use silicone impregnated into sea urchin skeleton to form a porous structure once the skeleton is dissolved away in U.S. Pat. Nos. 3,890,107 and 3,929,971.

An electrostatic spinning technology has been patented for use in primarily polyurethane grafts in U.S. Pat. Nos. 4,043,331; 4,044,404; 4,639,186; 4,127,706; 4,345,414; 4,323,525; and 4,878,908. These patents were used to spin polyurethane fibers. Without the addition of Infra Red (IR) curing as part of the immediate fiber curing process, the silicone fibers would meld together and form a clump.

SUMMARY OF THE INVENTION

The general purpose of the present invention is to provide a silicone/DACRON composite vascular graft for use as an artificial blood vessel, especially an arteriovenous (A-V) graft fistula providing long-term vascular access for kidney dialysis applications.

According to one embodiment of the present invention, there is provided a graft including a non-porous, smooth inner blood contact surface which reduces thrombus deposition; a silicone bead spiral or ring for anti-kink and anti-crush; a DACRON wind primarily for added strength; a small pore bulk construction with an impermeable inner surface which reduces fibroblast ingrowth and helps maintain compliance; continued elasticity allows excellent needle puncture sealing immediately and over time without applying external pressure; and the DACRON wind is coated with silicone to prevent body tissue from contacting DACRON which is a very thrombogenic material.

According to the process for the embodiment of the present invention, the use of IR energy partially cures the silicone strand before it contacts the mandrel; the order of construction of the graft enhances the strength, anti-crush, and anti-kink; the angle of applying the DACRON yarn and placement on top of the silicone bead allows the DACRON filaments to move relative to its repeat unit neighbor to help reduce any tendency toward graft kinking; and the silicone is dispersed in solvent for electrostatic spinning.

In another embodiment of the present invention, the blood contacting surface of the graft can be of a fibrous porous construction, similar but not necessarily identical, in structure to the middle and outer porous structure of the first embodiment. The pore size may range from approximately 2 microns to 100 microns. The porous inner surface will allow cellular attachment to the inside surface of the graft. These cells may originate from cells located at the junction of the graft with the native vessel, from cells that grow through the walls of the graft from the outside tissue or from the blood itself. The porous inner surface may enhance long term patency of the graft in vascular grafting situations where the blood flow rate is relatively low.

In yet another embodiment of the present invention, the graft can be constructed without the DACRON yarn filament. The function of the graft will be suitable for most vascular graft applications; the strength of the graft to resist aneurysm or suture pullout will be somewhat reduced.

The significant aspects, advantages and uniqueness of this graft in summary are: 1) the non-porous smooth silicone blood contact surface, which reduces thrombus deposit; 2) the bulk pore size and the solid inner surface, results in needle puncture sealing immediately and over time without applying external pressure; 3) the use of IR energy along with electrostatic spinning; 4) the application of a silicone bead for anti-kink and anti-crush; 5) the application of DACRON yarn for strength without any significant reduction in anti-kink properties of the graft; 6) the coating of the DACRON yarn with silicone prior to its application onto the graft; and 7) the bulk pore size and solid inner surface which tends to allow reticulocyte penetration into the porous portion of the graft, but not much fibroblastic ingrowth, results in retaining graft compliance or elasticity over time.

Another significant aspect and feature of the process is construction which uses electrostatic spinning or spraying technology to form a fibrous and porous silicone structure that is found in much of the graft wall. This electrostatic technology is also used to apply the non-porous smooth silicone layer directly onto a mandrel and form the blood contact surface after removal of the graft from the mandrel.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DESCRIPTION OF THE PREFERRED EMBODIMENTS

Figure 1:
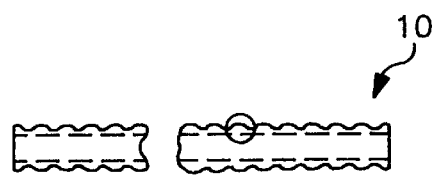
FIG. 1 illustrates a plan view of a vascular graft.

FIG. 1 illustrates a plan view of the graft 10.

Figure 2:
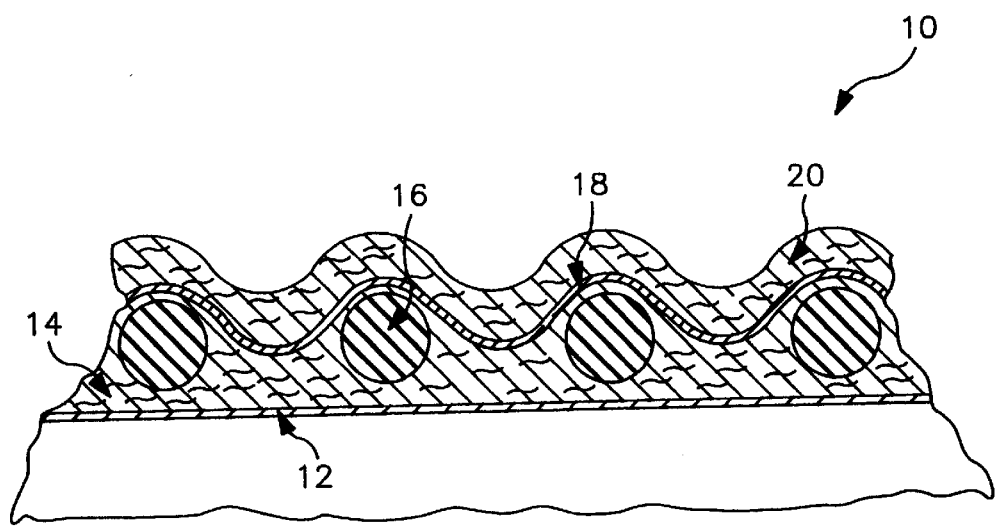
FIG. 2 illustrates a partial cross-sectional view of FIG. 1.
Figure 3:
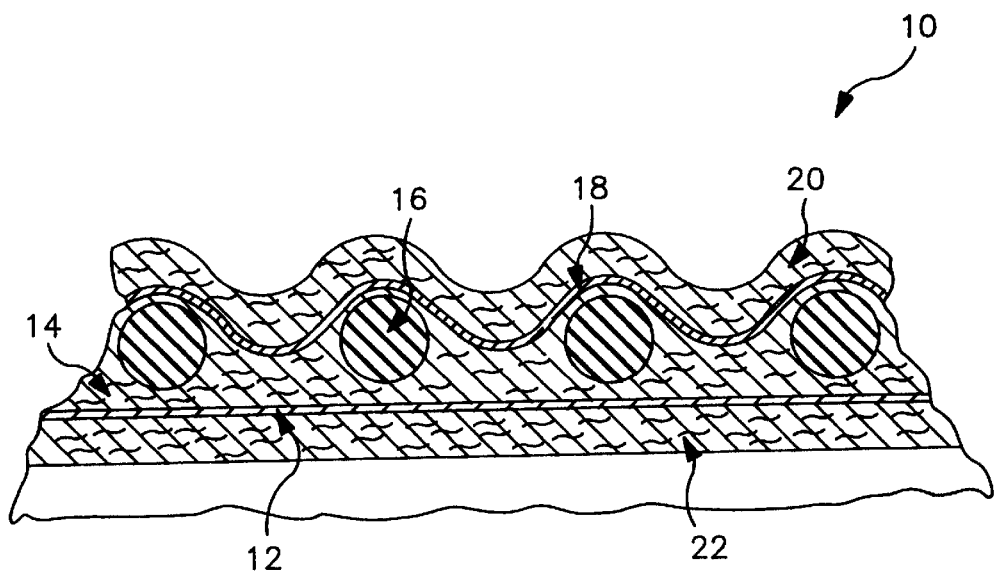
FIG. 3 illustrates a first alternative embodiment.
Figure 4:
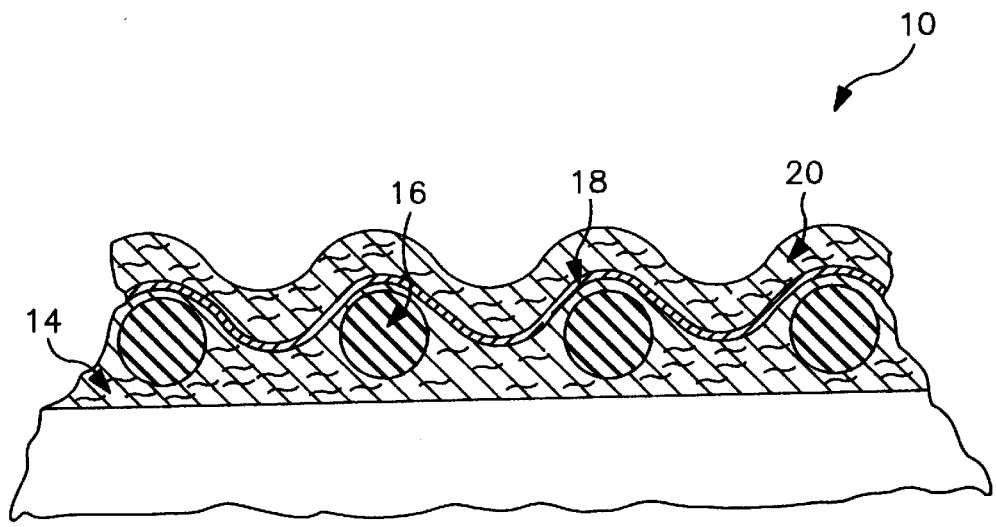
FIG. 4 illustrates a second alternative embodiment.

FIG. 2 illustrates a partial cross-sectional view of FIG. 1. A meld layer 12 is first applied to a mandrel spinning at low rpm (approximately 200 rpm) with IR heater off, but with the electrostatic spinning voltages of the grid and mandrel activated. This allows a uniform layer of silicone to be deposited onto the mandrel forming a blood contact surface that is as smooth as the mandrel finish and impermeable to blood, plasma, or cellular penetration. The high flow rate of blood which will move through the graft 10 will help prevent thrombus deposition on the smooth surface. Since blood or plasma cannot penetrate this layer, this graft 10 does not require preclotting (a method required for some porous grafts whereby blood is allowed to clot within the graft wall to prevent seepage or bleeding through the graft walls). This non-porous inner meld layer 12 also reduces the amount of fibroblastic cell penetration into the graft 10 from the outside surface. Fibroblastic ingrowth generally results in the deposition of collagen within the pores of porous grafts and significantly reduces the flexibility of the graft 10 over time. The reduction in fibroblastic ingrowth into the walls of this graft 10 allows it to remain flexible and thereby maintain its needle puncture hole sealing characteristic, as well as its flexibility and anti-kink properties.

The next layer, which is applied on top of the non-porous meld layer 12, is the porous silicone middle layer 14. To form individual fibers the mandrel is spun at a much faster rate (approximately 4000 rpm). The IR heater and the electrostatic voltages are both activated. The fibers are partially cured before they contact the mandrel due to the application of IR energy. The porosity or percent void fraction in a porous silicone structure of this layer can be controlled by adjusting the amount of fiber cure and the amount of melding of the fiber prior to deposition onto the mandrel. This layer provides fibrous structure of the graft 10 which serves as a framework to hold the silicone bead 16 and DACRON yarn 18 that is applied on top of it, and to allow a structure that can expand and compress, and thereby contribute to the anti-kink character of the graft 10. This layer also contributes to graft strength and needle puncture sealing. The pore spacing and silicone fiber diameter range from 2 to 100 microns with a generally random occurrence. The pore size is of appropriate size to allow reticulocyte penetration into the graft wall, but not so large as to allow entry access to significant fibroblast penetration. Reticulocytes are cells which can penetrate into the small pore spaces, but generally do not deposit significant collagenous material that can result in loss of graft elasticity and needle hole sealing characteristics.

A silicone bead 16 is then applied in a noncured form in a spiral configuration onto the porous middle layer 14 of the graft 10. This step is not done using electrostatics and involves simply extruding a silicone bead 16 onto a rotating graft 10 while moving transversely to form a spiral; the silicone bead 16 is then partially cured afterward. This spiral silicone bead 16 serves to enhance the graft 10 anti-kink and anti-crush properties by providing a structure which tends to maintain a circular cross section in the graft under compressive forces and forces which are generated when the graft 10 is bent to a radius of curvature of 1 cm or less. This spiral silicone bead 16 could be replaced with a series of torus shaped rings spaced approximately as far apart as each repeat unit of the spiral.

On top of the silicone bead, a polyethylene terethalate (PET) or DACRON winding 18 is applied forming a series of spirals which are wound with both right handedness and left handedness winding directions. The presence of the DACRON winding 18 provides strength to the graft 10 so that the graft 10 does not exhibit weakness axially or radially with resultant aneurysm formation. The DACRON fibers also contribute to enhance the pullout strength for sutures at the ends of the graft 10 where they are sewn to native vessels. The positioning of the DACRON winding 18 over the silicone bead 16 allows the graft 10 to maintain excellent anti-kink characteristics. Each DACRON strand can change its relative position to its neighboring repeat strand while the graft 10 is being bent, and thereby not inhibit bending. In addition, the presence of the DACRON strands in the graft wall tend to resist the formation of an oval cross section of the graft 10, and thereby contribute to enhanced anti-kink and anti-crush characteristics for the graft 10. The DACRON could be replaced by other biostable filamentous materials. Currently, the DACRON yarn is coated with silicone prior to its application onto the graft 10 to insure that DACRON material is not put into direct contact with body tissue and to enhance DACRON to graft bonding.

The outer silicone layer 20 is applied using ELS spinning and IR energy. It provides a porous outer layer that allows tissue to ingrow and anchor it in place in the subcutaneous tissue of the patient. It also helps to hold the DACRON winding 18 and silicone bead 16 in place. The pore structure is similar to the middle porous layer and retains its elasticity due to minimal fibroblastic ingrowth.

DESCRIPTION OF THE ALTERNATIVE EMBODIMENTS

The graft can be constructed in a manner identical with that of the preferred embodiment, however, with an additional porous silicone inner layer that is first applied onto the mandrel. This inner layer 22 will allow tissue to attach to the graft inner surface. A meld layer would then be applied second and would serve to prevent blood or plasma penetration through the graft wall.

In yet another embodiment, the graft is constructed in a manner identical to that of the preferred embodiment with the omission of the inner meld layer 12. With this construction, the inner surface consists of porous silicone fibers to allow good tissue attachment on the inner surface. In this case, the meld layer is not present and tissue can penetrate through the entire wall of the graft from the outside of the graft to the inner surface.

In yet another embodiment, the graft can be constructed of another biostable polymeric material, other than silicone, that can be spun electrostatically.

In yet another embodiment, the PET filament can be replaced by another biostable filament to provide additional graft strength.

In yet another embodiment, the silicone bead can be replaced by another biostable polymeric material that can be bound to silicone, and provide the anti-kink characteristics of the graft.

Various modifications can be made to the present invention without departing from the apparent scope hereof. There can be a coating or layer of the porous silicone middle layer material between the silicone bead and the polyethylene terethalate winding, although this is optional.

We claim:

1. A method of fabricating a fibrous porous tubular means for use a vascular graft comprising the steps of:
   a. electrostatically spinning a silicone polymeric material, forming fibers of said polymeric material;
   b. depositing said fibers onto a spinning mandrel and thereby forming a fibrous porous structure on said mandrel; and,
   c. providing controlled heating to cure said fibers using infra-red energy means.

2. The method of claim 1, further comprising the step of:
   a. controlling the porosity or percent void fraction of said fibrous porous structure by controlling the amount of fiber curing which occurs prior to deposition on said mandrel using infra-red energy means.

3. A method of fabricating a fibrous porous tubular means for use as a vascular graft comprising the steps of:
   a. applying a silicone layer impermeable to blood, plasma, or cellular penetration onto a mandrel;
   b. electrostatically spinning a silicone polymeric material, forming fibers of said polymeric material;
   c. spinning said mandrel and depositing said fibers onto said spinning mandrel and thereby forming a fibrous porous structure over said largely impermeable layer; and, d. providing controlled heating with infra-red energy to cure said fibers.

4. A method of fabricating a fibrous porous tubular means for use as a vascular graft comprising the steps of:
   a. electrostatically spinning a silicone polymeric material, forming fibers of said polymeric material;
   b. depositing said fibers onto a spinning mandrel and thereby forming a first layer of fibrous porous structure on said mandrel;
   c. providing controlled heating to cure said fibers through infra-red energy means;
   d. applying a silicone second layer impermeable to blood, plasma, or cellular penetration over said first layer; and,
   e. applying a third layer of fibrous porous structure in a manner similar to the first layer, thereby constructing a fibrous porous structure with an intervening layer impermeable to blood, plasma, or cellular penetration.

5. A method of fabricating a tubular means for use as a vascular graft with a silicone layer impermeable to blood, plasma, or cellular penetration comprising the steps of:
   a. electrostatically spinning a silicone polymeric material, forming fibers of said polymeric material;
   b. depositing said fibers onto a spinning mandrel to form a layer of said polymeric material on said mandrel;
   c. providing controlled heating of said fibers before said fibers contact said mandrel through infra-red energy means;
   d. using said controlled heating to provide controlled curing of said fibers and thereby to control the porosity of said layer of polymeric material on said mandrel; and,
   e. controlling the porosity of said layer to form a layer impermeable to blood, plasma, or cellular penetration.

6. A method for fabricating a fibrous porous tubular means for use as a vascular graft comprising the steps of:
   a. electrostatically spinning a silicone polymeric material, forming fibers of said polymeric material;
   b. depositing said fibers onto a spinning mandrel and thereby forming a fibrous porous structure on said mandrel;
   c. providing controlled heating of said fibers both before and after said fibers contact said mandrel through infra-red energy means;
   d. using said controlled heating to control the curing of said fibers before said fibers contact said mandrel;
   e. controlling the porosity or percent void fraction of said fibrous porous structure by controlling the amount of fiber curing which occurs prior to deposition on said mandrel;
   f. varying the porosity or percent void fraction in a controlled manner to form a structure with more than one layer so that different layers may have different porosity; and,
   g. controlling the porosity of at least one layer to form a layer impermeable to blood, plasma, or cellular penetration, thereby forming a structure with one or more porous layer(s) and one or more impermeable layer(s) as a single integral structure.

7. A method for fabricating a kink-resistant and crush-resistant fibrous porous structure for use as a vascular graft comprising the steps of:
   a. electrostatically spinning a silicone polymeric material, forming fibers of said polymeric material;
   b. depositing said fibers onto a spinning mandrel and thereby forming a fibrous porous structure on said mandrel;
   c. providing controlled heating to cure said fibers through infra-red energy means;
   d. controlling the porosity or percent void fraction of said fibrous porous structure by controlling the amount of fiber curing which occurs prior to deposition on said mandrel;
   e. subsequently applying a reinforcing bead onto said mandrel as either continuous helical bead or separate rings; and,
   f. curing the structure to form a fibrous porous structure with controlled porosity and external reinforcement.

8. A method for fabricating a kink-resistant and crush-resistant fibrous porous structure for use as a vascular graft comprising the steps of:
   a. electrostatically spinning a silicone polymeric material, forming fibers of said polymeric material;
   b. depositing said fibers onto a spinning mandrel and thereby forming a fibrous porous structure on said mandrel;
   c. providing controlled heating to cure said fibers through infra-red energy means;
   d. controlling the porosity or percent void fraction of said fibrous porous structure by controlling the amount of fiber curing which occurs prior to deposition on said mandrel;
   e. subsequently applying a reinforcing bead onto said mandrel as either continuous bead or separate rings;
   f. depositing additional fibers onto said mandrel over said reinforcing bead; and,
   g. curing the structure to form a fibrous porous structure with controlled porosity and reinforcement within the fibrous porous structure.

9. The method of claim 7 or 8, wherein said reinforcing bead is silicone or other biostable polymer.

10. The method of claim 7 or 8, wherein said reinforcing bead is chosen to be silicone to allow enhanced bonding and structural integrity.

11. The method of claim 7 or 8, further comprising the steps of:
    a. applying high-strength largely continuous fiber including but not limited to high-strength polymer yarn or high-strength fiber, said fiber oriented as helical winding with one or more wind angles, said fiber applied after and on top of said reinforcing bead.

12. A method for fabricating a strengthened fibrous porous structure for use as a vascular graft comprising the steps of:
    a. electrostatically spinning a silicone polymeric material, forming fibers of said polymeric material;
    b. depositing said fibers onto a spinning mandrel and thereby forming a fibrous porous structure on said mandrel;
    c. providing controlled heating to cure said fibers through infra-red energy means;
    d. controlling the porosity or percent void fraction of said fibrous porous structure by controlling the amount of fiber curing which occurs prior to deposition on said mandrel;
    e. subsequently applying largely continuous strengthening fiber onto said mandrel;
    f. said strengthening fiber oriented with circumferential component comprising a helical winding; and,
    g. curing the structure to form a fibrous porous structure with controlled porosity contained within external strengthening fibers.

13. A method for fabricating a strengthened fibrous porous structure for use as a vascular graft comprising the steps of:
   a. electrostatically spinning a silicone polymeric material, forming fibers of said polymeric material;
   b. depositing said fibers onto a spinning mandrel and thereby forming a fibrous porous structure on said mandrel;
   c. providing controlled heating using infra-red energy to cure said fibers;
   d. controlling the porosity or percent void fraction of said fibrous porous structure by controlling the amount of fiber curing which occurs prior to deposition on said mandrel;
   e. subsequently applying largely continuous strengthening fiber onto said mandrel;
   f. said strengthening fiber oriented with circumferential component such as helical winding;
   g. depositing additional electrostatically spun polymer fibers onto said mandrel over said strengthening fiber; and,
   h. curing the structure to form a fibrous porous structure with controlled porosity and strengthening fiber within the fibrous porous structure.

14. The method of claim 12 or 13, wherein said strengthening fiber includes but is not limited to a polyester yarn or other high-strength fiber.

15. The method of claim 12 or 13, wherein said strengthening fiber is coated with silicone to enhance bonding to the fibrous porous structure and to ensure that the strengthening fiber is not put into direct contact with body tissue.

16. The method of claim 15, further comprising the steps of:
   a. forming said fibrous porous structure in a not fully cured state;
   b. coating said strengthening fiber with a silicone coating material;
   c. applying said strengthening fiber and coating material while the coating material is in a not fully cured state; and,
   d. subsequently fully curing said fibrous porous structure and said coating material to provide enhanced bonding and structural integrity.

17. A method of fabricating a fibrous porous structure with multiple layers for use as a vascular graft comprising the steps of:
   a. electrostatically spinning a silicone polymeric material, forming fibers of said polymeric material;
   b. depositing said fibers onto a spinning mandrel and thereby forming a fibrous porous structure on said mandrel;
   c. providing controlled heating with infra-red energy of said fibers and before said fibers contact said mandrel;
   d. using said controlled heating to control the curing of said fibers before said fibers contact said mandrel;
   e. controlling the porosity or percent void fraction of said fibrous porous structure by controlling the amount of fiber curing which occurs prior to deposition on said mandrel;
   f. subsequently applying largely continuous strengthening fiber onto said mandrel; and,
   g. applying additional layers of material comprising a reinforcing bead, strengthening fiber, coating material, or additional fibrous porous layer(s) formed by varying the porosity or percent void fraction in a controlled manner to form a structure with more than one layer so that different layers may have different porosity.

18. A method for fabricating a fibrous porous structure for use as a vascular graft comprising the steps of:
   a. dispersing a silicone polymer in a suitable solvent which enhances the action of electrostatic forces when the dispersion is spun using electrostatic forces;
   b. electrostatically spinning said polymeric dispersion, forming fibers of said polymeric dispersion;
   c. depositing said fibers onto a spinning mandrel and thereby forming a fibrous porous structure on said mandrel; and,
   d. partially curing said fibers using infra-red energy.

19. The method of claim 18, further comprising the steps of:
   a. providing controlled heating of said fibers before said fibers contact said mandrel through infra-red or means; and,
   b. using said controlled heating to control the curing of said fibers before said fibers contact said mandrel; thereby controlling porosity or percent void fraction of the fibrous porous structure.

* * * * *